United States Patent [19]

Hamprecht et al.

[11] 4,343,648
[45] Aug. 10, 1982

[54] HERBICIDES

[75] Inventors: Gerhard Hamprecht, Weinheim; Rolf-Dieter Acker, Leimen; Bruno Wuerzer, Otterstadt, all of Fed. Rep. of Germany

[73] Assignee: BASF Aktiengesellschaft, Fed. Rep. of Germany

[21] Appl. No.: 251,921

[22] Filed: Apr. 7, 1981

[30] Foreign Application Priority Data

May 2, 1980 [DE] Fed. Rep. of Germany ....... 3016825

[51] Int. Cl.³ .................... C07D 285/00; A01N 43/72
[52] U.S. Cl. ........................................... 71/91; 544/7
[58] Field of Search ........................ 544/2, 3, 7; 71/91

[56] References Cited

U.S. PATENT DOCUMENTS

| 2,449,520 | 9/1943 | Walter | 544/7 |
| 2,454,261 | 11/1948 | Walter | 544/7 |
| 4,013,477 | 3/1977 | Kay | 544/7 |

FOREIGN PATENT DOCUMENTS

| 1946262 | 9/1969 | Fed. Rep. of Germany . |
| 2026625 | 5/1970 | Fed. Rep. of Germany . |
| 2508832 | 9/1975 | Fed. Rep. of Germany . |

Primary Examiner—John M. Ford
Attorney, Agent, or Firm—Keil & Witherspoon

[57] ABSTRACT 6H-1,2,4,6-Thiatriazine-1,1-dioxides of the formula

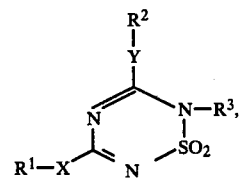

where
$R^1$ and $R^2$ are an aliphatic radical, a cycloaliphatic radical or a substituted aliphatic radical, $R^1$ may also be unsubstituted or substituted phenyl, unsubstituted or substituted benzyl, or tetrahydrofurylmethyl and $R^2$ may also be lower alkoxycarbo-lower alkoxy, lower alkylmercapto-carbo-lower alkoxy, lower alkoxy-carbo-lower alkylmercapto, lower alkylmercapto-carbo-lower alkylmercapto, unsubstituted or substituted aryl or unsubstituted or substituted benzyl,
$R^3$ is hydrogen, an aliphatic radical, a cycloaliphatic radical or substituted aliphatic radical,
$R^4$ and $R^5$ are lower alkyl and $R^5$ may also be hydrogen,
X and Y are oxygen, sulfur, sulfinyl or sulfonyl and
$X^1$ is oxygen or sulfur, and herbicides containing these compounds.

2 Claims, No Drawings

HERBICIDES

The present invention relates to novel 6H-1,2,4,6-thiatriazine-1,1-dioxides, processes for the preparation of these compounds, herbicides which contain these compounds, and the use of the compounds as herbicides.

The herbicidal action of substituted 6H-1,2,4,6-thiatriazin-5-one-1,1-dioxide derivatives is disclosed in German Laid-Open Application DOS No. 2,508,832.

We have found that substituted 6H-1,2,4,6-thiatriazine-1,1-dioxides of the general formula I

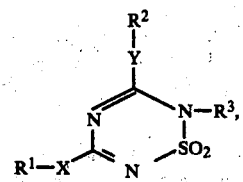

where
- $R^1$ and $R^2$ independently of one another are a saturated or unsaturated straight-chain aliphatic radical of 1 to 10 carbon atoms, a cycloaliphatic radical of 3 to 7 carbon atoms, a branched saturated or unsaturated aliphatic radical of 3 to 10 carbon atoms, a halogen-, alkoxy- or alkylmercapto-substituted aliphatic radical of 2 to 10 carbon atoms or a cycloalkoxy-substituted aliphatic radical of 4 to 10 carbon atoms,
- $R^1$ may also be unsubstituted or halogen, lower alkyl- or lower alkoxy-substituted phenyl, unsubstituted or halogen-substituted benzyl or tetrahydrofurylmethyl,
- $R^2$ may also be a halogen-, alkoxy-, dialkylketone- or alkylmercapto-substituted unsaturated aliphatic radical or a dialkylketone-substituted aliphatic radical of 3 to 10 carbon atoms, lower alkoxy-carbo-lower alkoxy, lower alkylmercapto-carbo-lower alkoxy, lower alkoxy-carbo-lower alkylmercapto, lower alkylmercapto-carbo-lower alkylmercapto, aryl which is unsubstituted or substituted by halogen, lower alkyl, halo-lower alkyl, lower alkoxy, halo-lower alkoxy, lower alkylmercapto halo-lower alkylmercapto, lower alkylsulfinyl, halo-lower alkylsulfinyl, lower alkylsulfonyl, halo-lower alkylsulfonyl, nitro, cyano, azido, carboxyl, SCN,

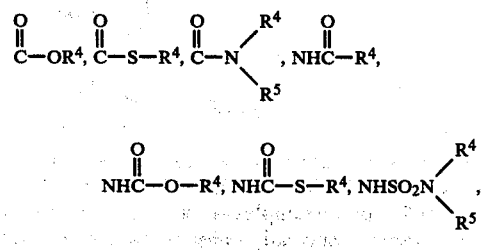

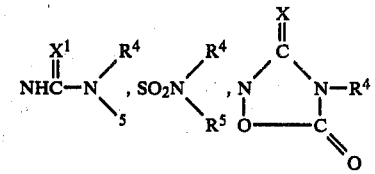

$SO_2OR^4$,

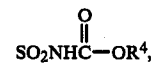

CH=NOH or CHO, or by lower alkoxy-carbo-lower alkoxy, lower alkylmercapto-carbo-lower alkoxy, lower alkoxy-carbo-lower alkylmercapto or lower alkylmercapto-carbo-lower alkylmercapto; $R^2$ may further denote benzyl which is unsubstituted or substituted by halogen, lower alkyl, halo-lower alkyl, lower alkoxy, halo-lower alkoxy or halo-lower alkylmercapto,
- $R^3$ is hydrogen, a straight-chain aliphatic radical of 1 to 10 carbon atoms, a cycloaliphatic radical of 3 to 7 carbon atoms, a branched aliphatic radical of 3 to 10 carbon atoms or halogen- or alkoxy-substituted alkyl of 2 to 10 carbon atoms,
- $R^4$ and $R^5$ are lower alkyl and $R^5$ may also be hydrogen,
- X and Y are oxygen, sulfur, sulfinyl or sulfonyl and
- $X^1$ is oxygen or sulfur have a powerful herbicidal action and are tolerated by various crop plants.

In formula I, $R^1$, $R^2$ and $R^3$ are, for example, methyl, ethyl, propyl, isopropyl, cyclopropyl, butyl, isobutyl, sec.-butyl, tert.-butyl, 1-pentyl, cyclopentyl, hexyl, cyclohexyl, 3-pentyl, 1,2-dimethylpropyl, 1,3-dimethylbutyl, 2-chloroethyl, 2-chloropropyl, 3-chloropropyl, 2-chloroisopropyl, 1-chloromethylpropyl, 1-ethyl-2-methylpropyl, 1,2,2-trimethylpropyl, 1,2-dimethylhexyl, 1-cyclohexylethyl, 2-chlorobut-3-yl, 2-chloro-2-methylpropyl, 2-fluorobut-3-yl, 2-fluoro-2-methylpropyl, 2-fluoroisopropyl, tert.-amyl, chloro-tert.-butyl, 2,2,2-trifluoroethyl, methoxyethyl, ethoxyethyl, 3-methoxypropyl, methoxyisopropyl, 3-methoxybutyl, 1-methoxy-but-2-yl, ethoxy-tert.-butyl, methoxy-tert.-butyl, 2-methoxy-butyl and 4-methoxy-butyl.

Further, $R^1$ and $R^2$ may be, for example, allyl, methallyl, crotyl, 2-ethylhex-2-en-1-yl, hex-5-en-1-yl, 2-methyl-but-2-en-1-yl, 2-methyl-but-1-en-3-yl, but-1-yn-3-yl, but-2-yn-1-yl, but-1-en-3-yl, propargyl, 2-methyl-but-1-en-4-yl, 2-methyl-but-2-en-4-yl, 3-methyl-but-1-en-3-yl, methylmercaptoethyl, ethylmercapto-ethyl, 3-methylmercapto-propyl, 3-methylmercapto-butyl, 1-methylmercapto-but-2-yl, methylmercapto-tert.-butyl, 2-methylmercapto-butyl, cyclohexoxy-ethyl, benzyl, 2,6-dichlorobenzyl, 2-chloro-6-fluorobenzyl, 2,6-difluorobenzyl, phenyl, 4-chlorophenyl, 3,4-dichlorophenyl, 4-tert.-butylphenyl, 4-methoxy-3-chlorophenyl, 4-methoxyphenyl, 2-methylphenyl and 2-methyl-4-chlorophenyl.

Further, $R^2$ may be, for example, 3-chloroprop-1-en-1-yl, 2-chloroprop-1-en-1-yl, 2-chloroprop-2-en-1-yl, chloropropargyl, 4-chloro-but-2-yn-1-yl, 4-chloro-but-1-yn-3-yl, 3-methoxy-prop-1-en-1-yl, 2-methoxy-prop-1-en-1-yl, 2-methoxy-prop-2-en-1-yl, methoxy-propargyl, 4-methoxybut-2-ynyl, 4-methoxy-but-1-yn-3-yl, 3-methylmercapto-prop-1-en-1-yl, 2-methylmercaptoprop-1-en-1-yl, pent-2-en-4-on-1-yl, propan-2-on-1-yl, o-, m- or p-trifluoromethylphenyl, o-, m- or p-chlorodifluoromethoxyphenyl, o-, m- or p-trifluoromethoxyphenyl, o-, m- or p-methylmercaptophenyl, o-, m- or p-trifluoromethylmercaptophenyl, o-, m- or p-methylsulfinylphenyl, o-, m- or p-trifluoromethylsulfinylphenyl, o-, m- or p-methylsulfonylphenyl, o-, m- or p-trifluoromethylsulfonylphenyl, o-, m- or p-nitrophenyl, o-, m- or p-cyanophenyl, o-, m- or p-azidophenyl, o-, m- or p-carboxyphenyl, o-, m- or p-thiocyanatophenyl, o-, m- or p-methoxycarbophenyl, o-m- or p-methylmercaptocarbophenyl, o-, m- or p-methylamidophenyl, o-, m- or p-dimethylamidophenyl, o-, m- or p-acetamidophenyl, o-, m- or p-methoxycarbamyl, o-, m- or p-methylmercaptocarbamyl, o-, m- or p-N'-methylsulfamido-N-phenyl, o-, m- or p-N',N'-dimethylsulfamido-N-phenyl, o-, m- or p-N'-methylureido-N-phenyl, o-, m- or p-N'-methylthioureido-N-phenyl, o-, m- or p-N',N'-dimethylureido-N-phenyl, o-, m- or p-N',N'-dimethylthioureido-N-phenyl, o-, m- or p-methylsulfamyl-phenyl, o-, m- or p-dimethylsulfamyl-phenyl, o-, m- or p-methoxysulfonylphenyl, o-, m- or p-methoxycarbamylsulfonylphenyl, o-, m- or p-N-hydroxylamino-benzylidene, o-, m- or p-methoxycarbonylmethoxyphenyl, o-, m- or p-methoxycarbonyl-methylmercaptophenyl, o-, m- or p-(α-methoxycarbonyl)-ethoxyphenyl with the radical

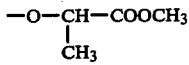

o-, m- or p(α-methoxycarbonyl)-ethylmercaptophenyl, o-, m- or p-methylmercapto-carbonylmethoxyphenyl, o-, m- or p-(α-methylmercaptocarbonyl)-ethoxyphenyl, 2-methyl-6-chlorobenzyl, o-, m- or p-chlorobenzyl, o-, m- or p-trifluoromethylbenzyl, o-, m- or p-trifluoromethoxybenzyl, o-, m- or p-chlorodifluoromethoxybenzyl, o-, m- or p-trifluoromethyl-mercaptobenzyl, 2-methyl-6-fluorobenzyl, 3,4-dichlorobenzyl, o-, m- or p-bromophenyl, 2,3-, 2,4-, 2,6-, 3,4- or 3,5-dichlorophenyl, 2,4,5-trichlorophenyl, 3,4-difluorophenyl, 3-chloro-4-fluorophenyl, 3-fluoro-4-chlorophenyl, 3-chloro-4-methoxyphenyl, 3-chloro-4-bromophenyl, 3-chloro-4-methylphenyl, o-, m- or p-isopropylphenyl, o-, m- or p-tert.-butylphenyl, 2,4-dinitrophenyl, 2-chloro-4-nitrophenyl, 2,4-dinitro-6-sec.-butylphenyl, 2,6-dibromo-4-cyanophenyl, 2,6-diiodo-4-cyanophenyl, 2,4-dinitro-6-methylphenyl, 3-carboxy-4-nitrophenyl, 2,4-dinitro-6-tert.-butylphenyl, o-, m- or p-formylphenyl, o-, m- or p-4'-methyl-1',2',4'-oxadiazolidin-2-yl-3',5'-dione, 2,4-dichloro-6-methylphenyl, 2-chloro-4-trifluoromethylphenyl and 3-methoxycarbo-4-nitrophenyl.

Further, we have found that the novel compounds are obtained in a simple manner by a method wherein a compound of the general formula II

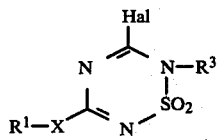

where $R^1$, X and $R^3$ have the above meanings and Hal is halogen, is reacted with a compound of the formula III

where $R^2$ and Y have the above meanings, or with an alkali metal salt, alkaline earth metal salt or ammonium salt of this compound, in the presence or absence of an inert organic solvent, and in the presence or absence of an acid acceptor, at from $-50°$ to $150°$ C., under atmospheric or superatmospheric pressure, continuously or batchwise.

If 5-chloro-6-isopropyl-3-methoxy-6H-1,2,4,6-thiatriazine-1,1-dioxide and propanol are used as starting materials, the course of the reaction can be represented by the following equation:

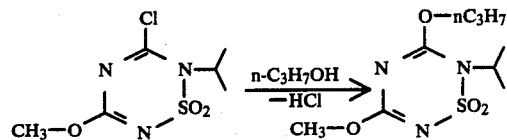

If 5-chloro-6-isopropyl-3-ethoxy-6H-1,2,4,6-thiatriazine-1,1-dioxide and sodium 4-chlorobenzenesulfinate are used, the course of the reaction can be represented by the following equation:

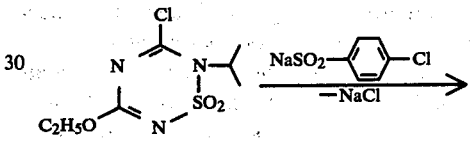

If 5-chloro-6-isopropyl-3-methylmercapto-6H-1,2,4,6-thiatriazine-1,1-dioxide and 2,4-dichlorophenol are used, the course of the reaction can be represented by the following equation:

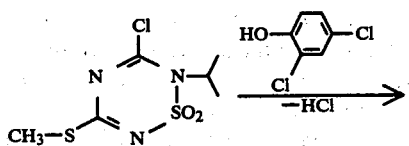

Advantageously, the reaction is carried out in a solvent or diluent which is insert under the particular reaction conditions. Examples of suitable solvents are halohydrocarbons, especially chlorohydrocarbons, e.g.

tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, m- and p-dibromobenzene, o-, m- and p-chlorotoluene and 1,2,4-trichlorobenzene; ethers, e.g. ethyl propyl ether, methyl tert.-butyl ether, n-butyl, ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta, \beta'$-dichlorodiethyl ether; nitrohydrocarbons e.g. nitromethane, nitroethane, nitrobenzene, o-, m- and p-chloronitrobenzene and o-nitrotoluene; nitriles, e.g. acetonitrile, butyronitrile, isobutyronitrile, benzonitrile and m-chlorobenzonitrile; aliphatic or cycloaliphatic hydrocarbons, e.g. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, e.g. ethyl acetate, ethyl acetoacetate and isobutyl acetate; amides, e.g. formamide, methylformamide and dimethylformamide; ketones, e.g. acetone and methyl ethyl ketone; and at times also water, and mixtures of the above. Advantageously, the solvent is used in an amount of from 100 to 2,000% by weight, preferably from 200 to 700% by weight, based on starting material II.

All conventional acid-binding agents can be used as the acid acceptors. Preferred examples are tertiary amines, alkaline earth metal compounds, ammonium compounds, alkali metal compounds and mixtures of these. However, zinc compounds may also be used. Specific examples of basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methyl-pyrrolidone, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline,β-picoline,γ-picoline,isoquinoline, pyrimidine, acridine, N,N,N',N'-tetramethylethylenediamine, N,N,N'N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

The acid acceptors are advantageously used in from 80 to 120% of the amount equivalent to the starting material II. However, the hydrogen halide formed can also be removed by sweeping with an inert gas, for example nitrogen.

The starting materials III required for the reaction are in general employed in from 80 to 120% of the amount equivalent to the starting material II. However, the starting material II may also be employed directly as the solvent. Alternatively, the starting material III can be initially introduced into one of the above diluents, after which the starting material II and an acid acceptor are added, simultaneously or in any order, through two separate lines.

An advantageous method of preparing the novel compounds is to take the starting material II, in the presence or absence of one of the above diluents, and then to add the starting material III and an acid.

In many cases, the reaction is complete immediately after addition of the components; if not, the mixture is stirred further for from 10 minutes to 10 hours at from −50° to 150° C., preferably from 0° to 120° C., especially from 20° to 100° C.

If an inert gas is used to remove the hydrogen halide, it is advantageous to stir the mixture, after addition of the components, for from 0.2 to 10 hours at from 40° to 100° C.

The end product I is isolated from the reaction mixture in a conventional manner, for example after distilling off the solvent or excess starting material III, or directly, by filtering off.

In the latter case, the residue is washed with water or dilute alkali to remove acidic impurities, and is dried. In the case of water-immiscible diluents, the reaction mixture can also be extracted direct with water or with dilute alkali, and then be dried and evaporated down. However, it is also possible to dissolve the residue from filtration in a water-immiscible solvent, and wash this solution as described. The desired end products are obtained in a pure form; if desired, they can be purified further by recrystallization, chromatograpy or distillation.

The methods which follow relate to the preparation of the starting compounds of the formula II, and to the compounds from which they themselves are prepared.

METHOD 1

198 parts by weight of methylaminosulfonyl chloride and 162 parts of triethylamine were introduced simultaneously, through 2 separate lines, into a stirred mixture of 202 parts of N-carbomethoxy-O-methylisourea in 1,570 parts of acetonitrile, at 25°–30° C. After 3 hours' stirring at 25° C., the hydrochloride which had precipitated was filtered off and the filtrate was evaporated down under reduced pressure. The residue was dissolved in 1,500 parts of 1,2-dichloroethane and the solution was extracted once with water and twice with 0.5 N hydrochloric acid. The extract was then dried over magnesium sulfate and evaporated down under reduced pressure, giving 257 parts of N-carbomethoxy-N'-methylsulfamyl-O-methylurea, of $n_D{}^{25}=1.4851$.

96 parts of this product were dissolved in 235 parts of absolutely dry methanol, 153.5 parts of a 30 percent strength by weight solution of sodium methylate in methanol were added, and the mixture was stirred under reflux for 3 hours. It was then evaporated down under reduced pressure, the residue was dissolved in water, and the solution was extracted once with ether and then acidified with dilute sulfuric acid. The product was filtered off, washed with water and dried, giving 68 parts (=82.5% of theory) of 6-methyl-3-methoxy-6H-1,2,4,6-thiatriazin-5-one-1,1-dioxide, of melting point 198°–202° C.

METHOD 2

37.9 parts of isopropylaminosulfonyl chloride and 26.3 parts of triethylamine were added simultaneously, through two separate lines, to a stirred mixture of 54 parts of N-carbomethoxy-S-benzyl-isothiourea in 740 parts of 1,2-dichloroethane, at 5°–10° C. After 4 hours' stirring at 25° C., the reaction mixture was extracted once with 200 parts of water and twice with 100 parts of 0.5 N hydrochloric acid at a time. The mixture was then dried and evaporated down under reduced pressure, giving 79 parts of N-carbomethoxy-N'-isopropylsulfamyl-S-benzylisothiourea, of $n_D^{25}=1.5598$. This material crystallized on trituration with hexane; melting point 76°–78° C. 76 parts of the N-carbomethoxy-N'-isopropylsulfamyl-S-benzyl-isothiourea obtained were dissolved in a mixture of 44 parts of 50 percent strength by weight sodium hydroxide solution and 200 parts of water, and the batch was stirred for 5 minutes at 85° C. It was then cooled and acidified with 15% strength hydrochloric acid, and the oil which precipitated was taken up in methylene chloride. The solution was dried over magnesium sulfate, filtered through neutral alumina and evaporated down under reduced pressure, giving 59.5 parts of 6-isopropyl-3-benzylmercapto-6H-1,2,4,6-thiatriazin-5-one-1,1-dioxide (86.3% of theory), of melting point 124°–130° C.

METHOD 3

59.6 parts of cyclohexylaminosulfonyl chloride and 26.9 parts of pyridine were introduced, through two separate lines, into a stirred solution of 39.6 parts of N-carbomethoxy-O-methyl-isourea in 300 parts of ethyl acetate, at 15°–20° C. After having been stirred for 4 hours at 25° C., the reaction mixture was extracted once with water and once with 0.5 N hydrochloric acid, dried and then evaporated down under reduced pressure. This gave 79 parts of N-carbomethoxy-N'-cyclohexylsulfamyl-O-methyl-isourea, of $n_D^{25}=1.4970$. After trituration with a small amount of ether, the compound crystallized; melting point 84°–86° C. 15 parts of the N-carbomethoxy-N'-cyclohexyl-sulfamyl-O-methyl-isourea obtained were dissolved in a mixture of 9 parts of 50 percent strength by weight sodium hydroxide solution and 20 parts of water and the reaction solution was stirred for 4 minutes at 55°–60° C. After cooling, it was extracted once with ether and then stirred into a mixture of 9.5 parts of concentrated hydrochloric acid in 10 parts of water. The product was filtered off, washed with water and dried, giving 9 parts of 6-cyclohexyl-3-methoxy-6H-1,2,4,6-thiatriazin-5-one-1,1-dioxide of melting point 173°–177° C.

METHOD 4

95 parts of isopropylaminosulfonyl chloride were stirred into a mixture of 96 parts of N-carbomethoxy-O-isopropyl-isourea and 73 parts of triethylamine in 700 parts of tetrahydrofuran at 10°–15° C., in the course of 25 minutes. After having been stirred for one hour at 25° C., the reaction mixture was extracted once with water and once with 0.5 N hydrochloric acid, dried and evaporated down under reduced pressure. 130 parts of N-carbomethoxy-N'-isopropylsulfamyl-O-isopropylisourea, of melting point 62°–64° C., were obtained. 33.7 parts of this product were cyclized with 17.6 parts of 50 percent strength by weight sodium hydroxide solution in 30 parts of water for 5 minutes at 55°–60° C. After extraction with ether, acidification, filtering, washing the residue with water and drying, 22 parts of 6-isopropyl-3-isopropoxy-6H-1,2,4,6-thiatriazin-5-one-1,1-dioxide, of melting point 164°–167° C., were obtained.

METHOD 5

12 parts of 6-isopropyl-3-isopropoxy-6H-1,2,4-thiatriazin-5-one-1,1-dioxide were dissolved in a mixture of 10.4 parts of a 30 percent strength by weight solution of sodium methylate in methanol and 64 parts of methanol at 25° C. After evaporating down, 13.8 parts of the 2-sodium salt of 6-isopropyl-3-isopropoxy-6H-1,2,4,6-thiatriazin-5-one-1,1-dioxide were obtained; melting point 123° C., with decomposition.

METHOD 6

140 parts of N-carboxymethyl-N'-methylsulfamyl-O-methyl-urea, in a mixture of 79.5 parts of sodium carbonate, 450 parts of water and 31 parts by volume of 2 N sodium hydroxide solution, were stirred for 10 minutes at 45° C. The reaction mixture was then cooled, extracted with ether, and stirred slowly into a mixture of 78 parts of concentrated sulfuric acid and 150 parts of ice water. The product was filtered off, washed with water and dried, giving 81 parts of 6-methyl-3-methoxy-6H-1,2,4,6-thiatriazin-5-one-1,1-dioxide (68% of theory), of melting point 195°–199° C.

METHOD 7

215 parts of 6-methyl-3-methoxy-6H-1,2,4,6-thiatriazin-5-one-1,1-dioxide were introduced into a stirred mixture of 275 parts of phosphorous pentachloride in 1,480 parts of phosphorus oxychloride at room temperature, and the batch was heated to 110° C. in the course of 30 minutes. After 4 hours' stirring under reflux, the reaction mixture was concentrated under reduced pressure, giving 235 parts (99.6% of theory) of 5-chloro-6-methyl-3-methoxy-6H-1,2,4,6-thiatriazine-1,1-dioxide, of melting point 77°–83° C.

METHOD 8

154 parts of phosphorus pentachloride were added, in the course of 2 minutes, to a stirred mixture of 128 parts of 6-ethyl-3-methoxy-6H-1,2,4,6-thiatriazin-5-one-1,1-dioxide in 840 parts of phosphorus oxychloride, at 25° C. The reaction mixture was stirred under reflux for 5½ hours and then concentrated under reduced pressure. The oil which remained was taken up in 300 parts of 1,2-dichloroethane and chromatographed over neutral alumina (activity I). The solution was then evaporated down, giving 127.5 parts (91% of theory) of 5-chloro-6-ethyl-3-methoxy-6H-1,2,4,6-thiatriazine-1,1-dioxide, of melting point 63°–70° C.

METHOD 9

50 parts of phosphorus pentachloride were introduced into a stirred mixture of 41.4 parts of 6-methyl-3-ethoxy-6H-1,2,4,6-thiatriazin-5-one-1,1-dioxide in 100 parts of 1,2-dichloroethane and 100 parts of phosphorus oxychloride at room temperature. The reaction mixture was stirred under reflux for 12 hours and then evaporated down under reduced pressure, giving 43.5 parts (96.5% of theory) of 5-chloro-6-methyl-3-ethoxy-6H-1,2,4,6-thiatriazine-1,1-dioxide, of melting point 75°–80° C.

METHOD 10

50 parts of phosphorus pentachloride were added to a stirred mixture of 44 parts of 6-n-propyl-3-methoxy-6H-1,2,4,6-thiatriazin-5-one-1,1-dioxide and 268 parts of phosphorus oxychloride at 22° C., and the batch was heated to 110° C. in the course of 20 minutes. After 7 hours' stirring under reflux, it was evaporated down under reduced pressure, giving 45 parts of oily 5-chloro-6-n-propyl-3-methoxy-6H-1,2,4,6-thiatriazine-1,1-dioxide; NMR (CDCl$_3$): N-CH$_2$ 4.0–4.28.

Distillation at 125°–130° C./0.01 mbar gave 40.3 parts (84% of theory) of pure product.

METHOD 11

A suspension of 25 parts of 6-ethyl-3-methylmercapto-6H-1,2,4,6-thiatriazin-5-one-1,1-dioxide in 2.5 parts of DMF and 245 parts of 1,2-dichloroethane, at 83° C., was gassed with phosgene for 14 hours, whilst stirring. It was then evaporated down under reduced pressure, giving 27 parts of a viscous oil, which according to the NMR spectrum contained about 45% of 5-chloro-6-ethyl-3-methylmercapto-6H-1,2,4,6-thiatriazine-1,1-dioxide. A sample was distilled at 136°–144° C./0.01 mbar; NMR (CDCl$_3$): N-CH$_2$ 4.04–4.42 δ (q), CH$_3$S 2.52 δ (s).

The Examples which follow relate to the preparation of the novel compounds.

EXAMPLE 1

6-Isopropyl-3-methoxy-5-ethoxy-6H-1,2,4,6-thiatriazine-1,1-dioxide (No. 1)

28.7 parts by weight of 5-chloro-6-isopropyl-3-methoxy-6H-1,2,4,6-thiatriazine-1,1-dioxide were added, a little at a time, in the course of 10 minutes, to a stirred mixture of 12.2 parts of triethylamine and 90 parts of absolute ethanol at 20°–25° C. After 3 hours' stirring at 25° C., the reaction mixture was evaporated down under reduced pressure, the residue was taken up in methylene chloride and the solution was washed with 10% strength sodium carbonate solution. After drying over magnesium sulfate, chromatography over alumina and evaporating down under reduced presure, 24 parts of 6-isopropyl-33-methoxy-5-ethoxy-6H-1,2,4,6-thiatriazine-1,1-dioxide, of melting point 81°–85° C. were obtained.

EXAMPLE 2

6-Methyl-3-methoxy-5-octadecyloxycarbo-methylmercapto-6H-1,2,4,6-thiatriazine-1,1-dioxide (No. 2)

34.5 parts of octadecyl mercaptoacetate in 45 parts of ethyl acetate, and 10.2 parts of triethylamine, were introduced simultaneously through 2 separate lines, in the course of 15 minutes, into a stirred mixture of 21.2 parts of 5-chloro-6-methyl-3-methoxy-6H-1,2,4,6-thiatriazine-1,1-dioxide in 90 parts of ethyl acetate at 20°–25° C. The reaction mixture was stirred for 1 hour at 25° C. and the precipitate was then filtered off and washed with water to remove the triethylamine hydrochloride, then with dilute sodium carbonate solution and then again with water. The organic filtrate was evaporated down and the residue was also washed as above. After drying, a total of 41 parts of 6-methyl-3-methoxy-5-octadecyloxycarbomethylmercapto-6H-1,2,4,6-thiatriazine-1,1-dioxide, of melting point 74°–80° C., were obtained.

EXAMPLE 3

6-Methyl-3-n-propoxy-5-p-nitrophenoxy-6H-1,2,4,6-thiatriazine-1,1-dioxide (No. 3)

13.9 parts of p-nitrophenol in 40 parts of methylene chloride, and 10.2 parts of triethylamine, were introduced simultaneously through 2 separate lines, in the course of 10 minutes, into a stirred solution of 23.9 parts of 5-chloro-6-methyl-3-n-propoxy-6H-1,2,4,6-thiatriazine-1,1-dioxide in 180 parts of methylene chloride at 20°–25° C. The reaction mixture was stirred under reflux for 3 hours, cooled, washed with water and then 3 times with dilute sodium hydroxide solution, dried over magnesium sulfate and evaporated down under reduced pressure. 31 parts of 6-methyl-3-n-propoxy-5-p-nitrophenoxy-6H-1,2,4,6-thiatriazine-1,1-dioxide, of melting point 129°–131° C., were obtained.

EXAMPLE 4

6-Methyl-3-ethoxy-5-allyloxy-6H-1,2,4,6-thiatriazine-1,1-dioxide (No. 166)

7 parts of allyl alcohol and 12.9 parts of 2,6-dimethylpyridine were introduced simultaneously through 2 separate lines, in the course of 6 minutes, into a stirred mixture of 22.6 parts of 5-chloro-6-methyl-3-ethoxy-6H-1,2,4,6-thiatriazine-1,1-dioxide in 140 parts of tetrahydrofuran at 25°–35° C. After having been stirred for 30 minutes at 50° C., the reaction mixture was evaporated down, the residue was taken up in methylene chloride and this solution was washed 3 times with 10% strength sodium carbonate solution. It was then dried over magnesium sulfate and evaporated down under reduced pressure, giving 14 parts of 6-methyl-3-ethoxy-5-allyloxy-6H-1,2,4,6-thiatriazine-1,1-dioxide, of melting point 56°–60° C.

The following novel compounds were obtained similarly.

| Compound no. | $R^1$ | X | Y | $R^2$ | $R^3$ | M.p.[°C.]/$n_D^{25}$ |
|---|---|---|---|---|---|---|
| 4 | CH$_3$ | O | O | CH$_3$ | H | |
| 5 | CH$_3$ | O | O | CH$_3$ | CH$_3$ | 100–104 |
| 6 | CH$_3$ | O | O | C$_2$H$_5$ | CH$_3$ | 108–112 |
| 7 | CH$_3$ | O | O | C$_2$H$_5$ | C$_2$H$_5$ | 77–80 |
| 8 | CH$_3$ | O | O | C$_2$H$_5$ | i-C$_3$H$_7$ | |
| 9 | CH$_3$ | O | O | CH$_2$—CH=CH$_2$ | C$_2$H$_5$ | 69–72 |
| 10 | CH$_3$ | S | O | CH$_3$ | CH$_3$ | 129–133 |
| 11 | CH$_3$ | S | S | CH$_3$ | CH$_3$ | |
| 12 | CH$_3$ | S | SO$_2$ | CH$_3$ | CH$_3$ | |

-continued

| Compound no. | R¹ | X | Y | R² | R³ | M.p.[°C.]/$n_D^{25}$ |
|---|---|---|---|---|---|---|
| 13 | CH₃ | O | O | CH₂—CH=CH₂ | H | |
| 14 | C₂H₅ | O | O | CH₃ | CH₃ | |
| 15 | C₂H₅ | O | S | C₂H₅ | CH₃ | |
| 16 | C₂H₅ | O | O | C₂H₅ | C₂H₅ | |
| 17 | C₂H₅ | O | O | CH₂—CH=CH₂ | C₂H₅ | |
| 18 | C₂H₅ | O | O | 1-Propyn-yl-3 | CH₃ | 78–81 |
| 19 | C₂H₅ | S | O | CH₂—CH=CH₂ | CH₃ | |
| 20 | C₂H₅ | O | S | CH₂—CH=CH₂ | CH₃ | |
| 21 | C₂H₅ | O | O | CH=CH—CH₂Cl | CH₃ | |
| 22 | C₂H₅ | O | S | CH=C(Cl)—CH₃ | CH₃ | |
| 23 | n-C₃H₇ | O | O | CH₂—CH₂—OCH₃ | CH₃ | |
| 24 | n-C₃H₇ | O | O | 1-Chloro-2-butyn-yl-4 | CH₃ | |
| 25 | i-C₃H₇ | O | O | 1-Methoxy-2-butyn-yl-4 | C₂H₅ | |
| 26 | CH₃ | O | O | 1-Methylmercapto-2-butyn-yl-4 | CH₃ | |
| 27 | n-C₃H₇ | O | O | 1-Chloro-3-buty-n-yl-2 | C₂H₅ | |
| 28 | CH₃ | O | S | CH₂—C(Cl)=CH₂ | CH₃ | |
| 29 | C₂H₅ | O | O | CH₂—CH=CH—C(O)—CH₃ | CH₃ | |
| 30 | CH₃ | O | O | CH₂—C(O)—CH₃ | CH₃ | |
| 31 | CH₃ | O | O | CH₂—CH₂—S—CH₃ | CH₃ | |
| 32 | i-C₃H₇ | O | O | CH₃ | CH₃ | |
| 33 | n-C₄H₉ | O | O | C₂H₅ | CH₃ | |
| 34 | sec-C₄H₉ | O | O | n-C₃H₇ | CH₃ | |
| 35 | tetrahydrofuranyl-CH₂ | O | O | CH₃ | CH₃ | |
| 36 | CH₃ | O | O | CH(CH₃)—CO₂C₂H₅ | CH₃ | 1.4829 |
| 37 | CH₃ | O | O | 4-CF₃—phenyl | CH₃ | |
| 38 | CH₃ | O | O | 3-OCHF₂—Phenyl | CH₃ | |
| 39 | CH₃ | O | S | 3-Chlorophenyl | CH₃ | |
| 40 | CH₃ | O | O | n-C₃H₇ | CH₃ | 50–54 |
| 41 | C₂H₅ | O | O | n-C₄H₉ | C₂H₅ | |
| 42 | CH₃ | O | O | 4-Methylmercaptophenyl | C₂H₅ | |
| 43 | CH₃ | O | O | 4-Methoxyphenyl | CH₃ | |
| 44 | CH₃ | O | O | CH₃ | C₂H₅ | 102–104 |
| 45 | i-C₃H₇ | O | S | CH₃ | CH₃ | |
| 46 | n-C₄H₉ | O | O | C₂H₅ | C₂H₅ | |
| 47 | CH₃ | O | S | CH₃ | CH₃ | 125–128 |
| 48 | CH₃ | O | O | 2-Butyn-yl-4 | CH₃ | |
| 49 | CH₃ | O | O | 1-Butyn-yl-3 | CH₃ | |
| 50 | C₂H₅ | S | O | 1-Butyn-yl-3 | CH₃ | |
| 51 | CH₃ | O | O | CH₂—CH=CH₂ | CH₃ | 55–57 |
| 52 | i-C₃H₇ | O | O | CH₂—C(O)—CH₃ | CH₃ | |
| 53 | CH₂—CH=CH₂ | O | O | CH₃ | CH₃ | |
| 54 | Propargyl | O | O | CH₃ | C₂H₅ | |
| 55 | CH₂—CH₂Cl | O | O | C₂H₅ | C₂H₅ | |
| 56 | Cyclohexyl | O | S | CH₃ | i-C₃H₇ | |
| 57 | 3-Chlorophenyl | O | O | CH₃ | CH₃ | |
| 58 | CH₃ | O | O | i-C₃H₇ | CH₃ | 73–77 |
| 59 | C₂H₅ | O | S | n-C₄H₉ | C₂H₅ | |
| 60 | n-C₃H₇— | O | O | C₂H₅ | CH₃ | 49–51 |
| 61 | CH₃ | O | O | 4-Methylphenyl | C₂H₅ | |
| 62 | CH₃ | O | O | 4-CF₃S—phenyl | CH₃ | |
| 63 | C₂H₅ | S | O | CH₃ | CH₃ | |
| 64 | C₂H₅ | O | O | C₂H₅ | i-C₃H₇ | 40–46 |

-continued

| Compound no. | R¹ | X | Y | R² | R³ | M.p.[°C]/$n_D^{25}$ |
|---|---|---|---|---|---|---|
| 65 | tert.C₄H₉ | S | O | CH₃ | CH₃ | |
| 66 | C₂H₅ | O | O | CH₃ | i-C₃H₇ | 74–78 |
| 67 | C₂H₅ | O | SO₂ | CH₃ | CH₃ | |
| 68 | CH₃—O—CH₂CH₂ | O | O | CH₃ | CH₃ | |
| 69 | C₂H₅ | O | O | C₂H₅ | CH₃ | 72–75 |
| 70 | C₆H₅—CH₂ | O | O | CH₃ | CH₃ | |
| 71 | 4-Chlorobenzyl | O | O | CH₃ | CH₃ | |
| 72 | 4-Methoxyphenyl | O | O | C₂H₅ | CH₃ | |
| 73 | i-C₃H₇ | O | O | CH₃ | n-C₃H₇ | 71–75 |
| 74 | CH₃ | S | O | CH₂—CH=CH₂ | CH₃ | 90–93 |
| 75 | CH₃ | O | S | 1-Propyn-yl-3 | CH₃ | |
| 76 | CH₃ | O | O | CH₃ | i-C₃H₇ | 108–111 |
| 77 | CH₃ | O | O | CH₃ | sec-C₄H₉ | |
| 78 | CH₃ | O | O | C₂H₅ | tert.-C₄H₉ | |
| 79 | CH₃ | O | O | 1-Propyn-yl-3 | H | |
| 80 | C₂H₅ | O | O | CH₂—CH=CHC(=O)—CH₃ | C₂H₅ | |
| 81 | CH₃—S—CH₂CH₂ | O | O | CH₃ | CH₃ | |
| 82 | CH₃ | O | O | CH₂—CH=CH₂ | CH₂—CH=CH₂ | |
| 83 | CH₃ | S | O | CH₃ | CH₂—CH=CH₂ | |
| 84 | CH₃ | O | O | CH₃ | Cyclohexyl | |
| 85 | i-C₃H₇ | S | O | CH₃ | Cyclohexyl | |
| 86 | CH₃ | O | O | CH₃ | CH₂O—CH₃ | |
| 87 | CH₃ | O | O | CH₃ | CH₂—CH₂Cl | |
| 88 | C₂H₅ | O | O | CH₃ | CH₂—CH₂F | |
| 89 | CH₃ | O | O | 4-Nitrophenyl | CH₃ | 235–240 |
| 90 | CH₃ | O | O | —C₆H₄—SOCH₃ | CH₃ | |
| 91 | C₂H₅ | S | O | —C₆H₄—SO₂CF₃ | CH₃ | |
| 92 | C₂H₅ | O | O | 4-Cyanophenyl | CH₃ | |
| 93 | CH₃ | O | O | 4-Thiocyanophenyl | CH₃ | |
| 94 | i-C₃H₇ | O | O | 3-Carboxyphenyl | CH₃ | |
| 95 | CH₃ | O | O | 4-Nitro-3-carboxyphenyl | CH₃ | |
| 96 | CH₃ | O | O | 2-Methyl-4,6-dinitrophenyl | CH₃ | 160–163 |
| 97 | C₂H₅ | O | S | 4-Nitrophenyl | CH₃ | |
| 98 | n-C₃H₇ | O | O | —C₆H₄—SO₂CH₃ | CH₃ | |
| 99 | CH₃ | O | O | 2,4-Dichlorophenyl | CH₃ | 189–194 |
| 100 | CH₃ | O | O | 3,5-Dichlorophenyl | C₂H₅ | |
| 101 | CH₃ | O | O | 2,3-Dichlorophenyl | n-C₃H₇ | |
| 102 | CH₃ | O | S | —C₆H₄—CO₂CH₃ | CH₃ | |
| 103 | CH₃ | O | O | 2,4,6-Trichlorophenyl | CH₃ | 221–226 |
| 104 | CH₃ | S | O | —C₆H₄—C(=O)—SCH₃ | CH₃ | |
| 105 | C₂H₅ | O | O | —C₆H₄—C(=O)—NHCH₃ | C₂H₅ | |
| 106 | CH₃ | S | O | —C₆H₄—C(=O)—N(CH₃)₂ | CH₃ | |
| 107 | CH₃ | O | O | 2,4-Dinitro-6-tert-butylphenyl | CH₃ | 156–161 |

-continued

| Compound no. | R¹ | X | Y | R² | R³ | M.p.[°C.]/$n_D^{25}$ |
|---|---|---|---|---|---|---|
| 108 | $CH_2=CH-CH_2$ | O | O | —⟨phenyl⟩—$NHCO_2CH_3$ (meta) | $C_2H_5$ | |
| 109 | i-$C_3H_7$ | O | O | —⟨phenyl⟩—$NHCO_2CH_3$ (para) | $CH_3$ | |
| 110 | $CH_3$ | O | O | 2,4-dinitro-3-methyl-5-(sec-butyl)phenyl ($NO_2$, $NO_2$, $CH_3$, $CH_3-CH(C_2H_5)$) | $CH_3$ | 151–156 |
| 111 | n-$C_3H_7$ | O | O | —⟨phenyl⟩—$NHC(O)SCH_3$ | $CH_3$ | |
| 112 | $CH_3$ | S | O | —⟨phenyl⟩—$NHSO_2NHCH_3$ | $CH_3$ | |
| 113 | $CH_3$ | O | O | 2,6-Dibromo-4-cyanophenyl | $CH_3$ | 242–246 |
| 114 | $C_2H_5$ | O | O | —⟨phenyl⟩—$NHSO_2N(CH_3)_2$ | $C_2H_5$ | |
| 115 | $CH_3$ | O | O | —⟨phenyl⟩—CHO | $C_2H_5$ | |
| 116 | $C_2H_5$ | S | O | Benzyl | $CH_3$ | |
| 117 | $CH_3$ | O | O | 2,6-Diiodo-4-cyanophenyl | $CH_3$ | 276–281 |
| 118 | $CH_3$ | O | O | 2-Nitrophenyl | $C_2H_5$ | |
| 119 | $CH_3$ | O | O | 3-Nitrophenyl | $CH_3$ | 213–218 |
| 120 | $C_2H_5$ | O | O | —⟨phenyl⟩—CH=NOH | $CH_3$ | |
| 121 | $CH_3$ | S | O | —⟨phenyl⟩—$SO_3CH_3$ | $CH_3$ | |
| 122 | $C_2H_5$ | O | O | —⟨phenyl⟩—$SO_2N(CH_3)_2$ | $CH_3$ | |
| 123 | $CH_3$ | O | O | 4-Chlorophenyl | $CH_3$ | 199–202 |
| 124 | $CH_3$ | O | O | —⟨phenyl⟩—$OCH_2CO_2H$ | i-$C_3H_7$ | |
| 125 | $C_2H_5$ | S | O | —⟨phenyl⟩—$OCH_2CO_2CH_3$ | $CH_3$ | |
| 126 | $CH_3$ | O | O | 4-Nitrophenyl | $C_2H_5$ | 176–178 |

-continued

| Compound no. | R¹ | X | Y | R² | R³ | M.p.[°C.]/$n_D^{25}$ |
|---|---|---|---|---|---|---|
| 127 | CH₃ | S | O | —⟨⟩—SCH₂CO₂CH₃ | CH₃ | |
| 128 | C₂H₅ | O | O | —⟨⟩—SCH₂C(O)—SCH₃ | CH₃ | |
| 129 | CH₃ | O | O | 4-tert.-butylphenyl | CH₃ | 155–158 |
| 130 | C₂H₅ | O | S | 2,6-Dimethylphenyl | CH₃ | |
| 131 | CH₃ | O | O | 4-Chlorobenzyl | CH₃ | |
| 132 | CH₃ | O | O | 4-Cyanophenyl | CH₃ | 219–221 |
| 133 | CH₃ | O | O | 3,4-Difluorophenyl | CH₃ | |
| 134 | CH₃ | O | O | 3-tert.-butylphenyl | CH₃ | 113–116 |
| 135 | C₂H₅ | O | O | 4-tert.-butylphenyl | CH₃ | |
| 136 | CH₃ | O | O | 2,4-Dichloro-6-methyl-phenyl | CH₃ | 194–196 |
| 137 | C₂H₅ | O | O | 2-Chloro-4-nitrophenyl | CH₃ | |
| 138 | CH₃ | O | O | 4-Nitrophenyl | H | |
| 139 | CH₃ | O | O | 4-CF₃—2-chlorophenyl | CH₃ | 178–179 |
| 140 | CH₃ | O | O | 3-Chloro-4-methoxyphenyl | H | |
| 141 | C₂H₅ | O | O | 3-CF₃—phenyl | H | |
| 142 | CH₃ | O | O | —⟨⟩—NHCO₂CH₃ | CH₃ | 199–204 |
| 143 | CH₃ | O | O | —⟨⟩—NHC(O)—NHCH₃ | CH₃ | 216–220 |
| 144 | CH₃ | O | O | —⟨⟩—O—CH(CH₃)—CO₂CH₃ | CH₃ | 134–138 |
| 145 | CH₃ | S | O | 3,4-Dichlorobenzyl | CH₃ | |
| 146 | C₂H₅ | O | O | 4-Nitrophenyl | CH₃ | 146–150 |
| 147 | i-C₃H₇ | O | O | 2-Chloro-4-nitrophenyl | CH₃ | |
| 148 | C₂H₅ | O | O | 4-Nitrophenyl | i-C₃H₇ | 150–154 |
| 149 | CH₃ | O | O | —⟨⟩(NO₂)(CO₂CH₃) | CH₃ | |
| 150 | sec.C₄H₉ | O | O | 4-Nitrophenyl | i-C₃H₇ | 138–144 |
| 151 | C₂H₅ | O | S | Benzyl | CH₃ | |
| 152 | CH₃ | O | O | 4-Nitrophenyl | i-C₃H₇ | 200–204 |
| 153 | CH₃ | O | O | 4-Nitrophenyl | n-C₃H₇ | 152–155 |
| 154 | CH₃ | S | O | Benzyl | CH₃ | |
| 155 | CH₃ | O | O | Benzyl | CH₃ | 141–145 |
| 156 | CH₃ | O | O | 3-CF₃O—Phenyl | CH₃ | |
| 157 | CH₃ | O | O | sec.-Butyl | CH₃ | 1.4904 |
| 158 | CH₃ | O | O | 1-Propyn-yl-3 | CH₃ | 98–102 |
| 159 | CH₃ | O | O | 1-Propyn-yl-3 | C₂H₅ | |
| 160 | C₂H₅ | O | O | 1-Propyn-yl-3 | C₂H₅ | |
| 161 | C₂H₅ | O | O | Benzyl | CH₃ | 73–75 |
| 162 | CH₃ | O | O | 2,6-Dichlorobenzyl | CH₃ | 104–107 |
| 163 | n-C₃H₇ | O | O | CH₂—CH=CH₂ | CH₃ | 43–47 |
| 164 | n-C₃H₇ | O | O | 1-Propyn-yl-3 | CH₃ | 98–103 |
| 165 | C₂H₅ | O | O | 2,6-Dichlorbenzyl | CH₃ | 119–123 |
| 166 | C₂H₅ | O | O | Allyl | CH₃ | 56–60 |

The novel active ingredients can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g., ethanolamine, dimethylformamide, and water; solid carriers, for example natural rock powders, e.g., kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

To initiate the herbicidal action, wetting agents, adherents, and non-phytotoxic oils and oil concentrates may be added.

The herbicidal agents in general contain from 0.1 to 95% by weight of active ingredients, preferably from 0.5 to 90%.

The application rates depend on the composition and growth stages of the weed flora, and vary from 0.1 to 15, and preferably from 0.2 to 5.0, kg of active ingredients per hectare, the higher rates being used for total plant destruction.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting or watering.

Examples of such formulations are given below.

I. 90 parts by weight of the compound of Example 1 is mixed with 10 parts by weight of N-methyl-α-pyrrolidone. A mixture is obtained which is suitable for application in the form of very fine drops.

II. 80 parts by weight of the compound of Example 2 is mixed with 20 parts by weight of cyclohexanone. The composition may be sprayed as fine drops.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 3 parts by weight of the compound of Example 2 is intimately mixed with 97 parts by weight of particulate kaolin. A dust is obtained containing 3% by weight of the active ingredient.

V. 30 parts by weight of the compound of Example 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VI. 20 parts of the compound of Example 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

It may also be useful to apply the active ingredients, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies.

The influence of representatives of the novel, herbicidal, substituted 6H-1,2,4,6-thiatriazine-1,1-dioxides on the growth of unwanted and crop plants is demonstrated in greenhouse experiments.

The vessels employed were plastic flowerpots having a volume of 300 cm$^3$, and which were filled with a sandy loam containing about 1.5% humus. To ensure good growth of *Cyperus esculentus, Glycine max.* and *Oryza sativa,* peat was added. The seeds of the test plants given in Table 1 were sown shallow, and separately, according to species. In the case of *Cyperus esculentus,* pregerminated tubers were employed. In the preemergence treatment, the active ingredients were immediately applied to the surface of the soil as a suspension or emulsion in water by spraying through finely distributing nozzles.

The application rates varied, depending on the active ingredient. Rates employed were 0.5, 1.0, 2.0 and 4.0 kg of active ingredient per hectare.

After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which were sown directly in the pots and grew there were selected, or plants which were grown separately as seedlings and transplanted to the experiment vessels a few days before treatment. The amounts of active ingredient applied in this treatment also differed from ingredient to ingredient, and were either 0.5, 1.0 or 2.0 kg/ha.

The agent used for comparison purposes was compound A:

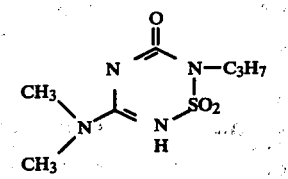

(disclosed in German Laid-Open Application DE-OS 2,508,832).

No cover was placed on the vessels in the postemergence treatment. The pots were set up in the greenhouse - species from warmer areas at from 20° to 35° C., and species from moderate climates at 10° to 20° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The results show that the novel compounds according to the invention are suitable for combating broadleaved unwanted plants and annual and perennial Cyperaceae in crop plants, or for total elimination of vegetation either on pre- or postemergence treatment. That the compounds are also effective against unwanted grasses is worthy of note.

TABLE 1

List of plant names

| Botanical name | Common name |
|---|---|
| Chenopodium album | lambsquarters |
| Cyperus spp. (C. iria, C. ferax, C. difformis) | annual sedges |
| Cyperus esculentus | yellow nutsedge |
| Datura stramonium | jimson weed |
| Glycine max | soybeans |
| Gossypium hirsutum | cotton |
| Matricaria spp. | chamomile spp. |
| Nicandra physaloides | apple of Peru |
| Oryza sativa | rice |
| Solanum nigrum | black nightshade |
| Zea mays | Indian corn, maize |

In an experiment to test the herbicidal action (postemergence application in the greenhouse), new compounds 51, 146 and 69 exhibited, at rates of 0.5 to 1.0 kg/ha, a better selective herbicidal action than the prior art compound A.

In an experiment to control unwanted broadleaved plants in soybeans (preemergence application in the greenhouse), new compounds 113, 36, 142, 119, 129, 136, 139 and 123 exhibited, at rates of 0.5 and 1.0 kg/ha, a better selective herbicidal action than prior art compound A.

In an experiment to control Cyperaceae in rice (preemergence treatment in the greenhouse), new compounds 40, 92, 144, 69, 89 and 155 exhibited, at rates of 4.0 and 2.0 kg/ha, a good selective herbicidal action.

In an experiment to test the selective control of broadleaved unwanted plants in crops (preemergence treatment in the greenhouse), new compounds 143, 144, 139 and 110 exhibited, at rates of 1.0 and 2.0 kg/ha, a good selective herbicidal action.

Compounds 89 and 155, for instance, also had an excellent action for the selective control of Cyperus esculentus in rice (postemergence application in the greenhouse).

If certain crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment). In view of the good tolerance of the active ingredients and the many application methods possible, the agents according to the invention, or mixtures containing them, may be used not only on the crop plants listed in Table 1, but also in a much larger range of crops for removing unwanted plants. Application rates may vary from 0.1 to 15 kg/ha and more.

The following crop plants may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of activity and to achieve synergistic effects, the novel active ingredients may be mixed among themselves or with numerous representatives of other herbicidal or growth-regulating active ingredient groups and applied in such mixtures. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone 5-methylamino-4-chloro-2-(3-trifluoromethylphenyl)-3(2H)-pyridazinone
5-methylamino-4-chloro-2-(3-$\alpha,\alpha,\beta,\beta$-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone 3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide N-(1-ethylpropyl)-2,6-dinitro-3,4-dimethylaniline
N-(1-methylethyl)-N-ethyl-2,6-dinitro-4-trifluoromethylaniline
N-n-propyl-N-$\beta$-chloroethyl-2,6-dinitro-4-trifluoromethylaniline
N-n-propyl-N-cyclopropylmethyl-2,6-dinitro-4-trifluoromethylaniline
N-bis-(n-propyl)-2,8-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-($\beta$-chloroethyl)-2,6-dinitro-4-methylaniline
N-ethyl-N-(2-methylallyl)-2,6-dinitro-4-trifluoromethylaniline
3,4-dichlorobenzyl N-methylcarbamate 2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(n-phenylcarbamoyl)-propanone oxime
N-ethyl-2-(phenylcarbamoyl)-oxypropionic acid amide
3'-N-isopropylcarbamoyloxypropionanilide ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate n-propyl N-ethyl-N-n-butylthiolcarbamate
2-chloroallyl N,N-dimethyldithiocarbamate
N-methyldithiocarbamic acid, sodium salt
triichloroacetic acid, sodium salt
α,α-dichloropropionic acid, sodium salt
α,α-dichlorobutyric acid, sodium salt
α,α-β,β-tetrafluoropropionic acid, sodium salt α-methyl-α,β-dichloropropionic acid, sodium salt methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)

O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate 2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine 2-azido-4-methylamino-6-isopropylamino-1,3,5-triazine
2-methylthio-4-ethylamino-6-isopropylamino-1,3,5-triazine 2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione 3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide 2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(2-n-propoxyethyl)-2-chloroacetanilide 2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt 2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione 2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyldimethylaminosulfate 2-ethoxy-2,3-dihydro-3,3-didmethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate 2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3,-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide 1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)

1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione 2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
0,0-diisopropyl-5-(2-benzosulfonylaminoethyl)-phosphorodithionate
2,3-dihydro-5,6-dimethyl-1,4-dithiin-1,1,4,4-tetraoxide 5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3-ethoxycarbonyl-4'-nitrophenyl ether
1-(4-benzoyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3(ethoxycarbonyl)-methylthio-4-nitrophenyl ether
2,4,6-trichlorophenyl-3'-(ethoxycarbonyl)-methylthio-4-nitrophenyl ether
2-[1-(N-ethoxyamino)-butylidene]-5-(2-ethylthiopropyl)-3-hydroxy-cyclohex-2-en-1-one (salts)
2-[1-(N-ethoxyamino)-butylidene]-5-(2-phenylthiopropyl)-3-hydroxy-cyclohex-2-en-1-one (salts)
4-[4-(4'-trifluoromethyl)-phenoxy]-pentene-2-carboxylic acid ethyl ester
2-chloro-4-trifluoromethyl-3'-methoxycarbonyl-4'-nitrophenyl ether
2,4-dichlorphenyl-3'-carboxy-4'-nitrophenyl ether (salts)

4,5-dimethoxy-2-(3-α,α,β-trifluoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1(3-chloro-4-ethoxyphenyl)-3,3-dimethylurea
ethyl 2-methyl-4-chlorophenoxythioacetate.

We claim:
1. A 6H-1,2,4,6-thiatriazine-1,1-dioxide of the formula

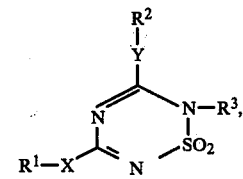

ps where
R$^1$ and R$^2$ independently of one another are a saturated or unsaturated straight-chain aliphatic radical of 1 to 10 carbon atoms, a cycloaliphatic radical of 3 to 7 carbon atoms, a branched saturated or unsaturated aliphatic radical of 3 to 10 carbon atoms, a halogen-, alkoxy- or alkylmercapto-substituted aliphatic radical of 2 to 10 carbon atoms or a cycloalkoxy-substituted aliphatic radical of 4 to 10 carbon atoms, R$^1$ may also be unsubstituted or halogen-, lower alkyl- or lower alkoxy-substituted phenyl, unsubstituted or halogen-substituted benzyl or tetrahydrofurylmethyl, R$^2$ may also be a halogen-, alkoxy-, dialkylketone- or alkylmercapto-substituted unsaturated aliphatic radical or a dialkylketone-substituted aliphatic radical of 3 to 10 carbon atoms, lower alkoxy-carbo-lower alkoxy, lower alkylmercapto-carbo-lower alkoxy, lower alkoxy-carbo-lower alkylmercapto, lower alkylmercapto-carbo-lower alkylmercapto, aryl which is unsubstituted or substituted by halogen, lower alkyl, halo-lower alkyl, lower alkoxy, halo-lower alkoxy, lower alkylmercapto, halo-lower alkylmercapto, lower alkylsulfinyl, halo-lower alkylsulfinyl, lower alkylsulfonyl, halo-lower alkylsulfonyl, nitro, cyano, azido, carboxyl, SCN,

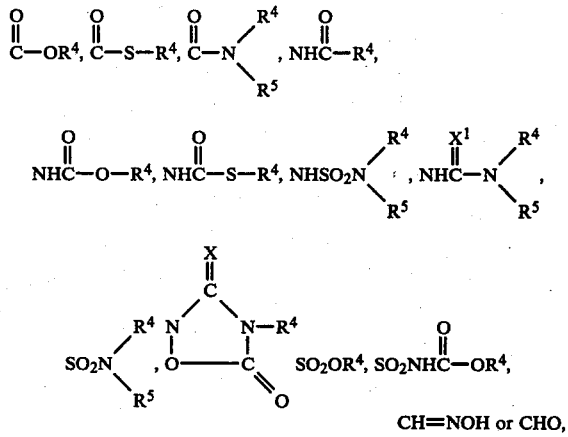

CH=NOH or CHO, or by lower alkoxy-carbo-lower alkoxy, lower alkylmercapto-carbo-lower alkoxy, lower alkoxy-carbo-lower alkylmercapto or lower alkylmercapto-carbo-lower alkylmercapto; or $R^2$ may also denote benzyl which is unsubstituted or substituted by halogen, lower alkyl, halo-lower alkyl, lower alkoxy, halo-lower alkoxy or halo-lower alkylmercapto, $R^3$ is hydrogen, a straight-chain aliphatic radical of 1 to 10 carbon atoms, a cycloaliphatic radical of 3 to 7 carbon atoms, a branched aliphatic radical of 3 to 10 carbon atoms or halogen- or alkoxy-substituted alkyl of 2 to 10 carbon atoms, $R^4$ and $R^5$ are lower alkyl and $R^5$ may also be hydrogen, X and Y are oxygen, sulfur, sulfinyl or sulfonyl and $X^1$ is oxygen or sulfur.

2. A process for combating the growth of unwanted plants, which comprises applying to the plants or the locus of the plants a herbicidally effective amount of a 6H-1,2,4,6-thiatriazine-1,1-dioxide of the formula

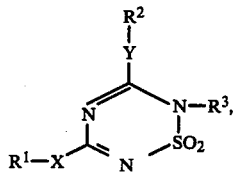

I where
$R^1$ and $R^2$ independently of one another are a saturated or unsaturated straight-chain aliphatic radical of 1 to 10 carbon atoms, a cycloaliphatic radical of 3 to 7 carbon atoms, a branched saturated or unsaturated aliphatic radical of 3 to 10 carbon atoms, a halogen-, alkoxy- or alkylmercapto-substituted aliphatic radical of 2 to 10 carbon atoms or a cycloalkoxy-substituted aliphatic radical of 4 to 10 carbon atoms, $R^1$ may also be unsubstituted or halogen-, or lower alkyl- or lower alkoxy-substituted phenyl, unsubstituted or halogen-substituted benzyl or tetrahydrofurylmethyl, $R^2$ may also be a halogen-, alkoxy-, dialkylketone- or alkylmercapto-substituted unsaturated aliphatic radical or a dialkylketone-substituted aliphatic radical of 3 to 10 carbon atoms, lower alkoxy-carbo-lower alkoxy, lower alkylmercapto-carbo-lower alkoxy, lower alkoxy-carbo-lower alkylmercapto, lower alkylmercapto-carbo-lower alkylmercapto, aryl which is unsubstituted or substituted by halogen, lower alkyl, halo-lower alkyl, lower alkoxy, halo-lower alkoxy, lower alkylmercapto halo-lower alkylmercapto, lower alkylsulfinyl, halo-lower alkylsulfinyl, lower alkylsulfonyl, halo-lower alkylsulfonyl, nitro, cyano, azido, carboxyl, SCN,

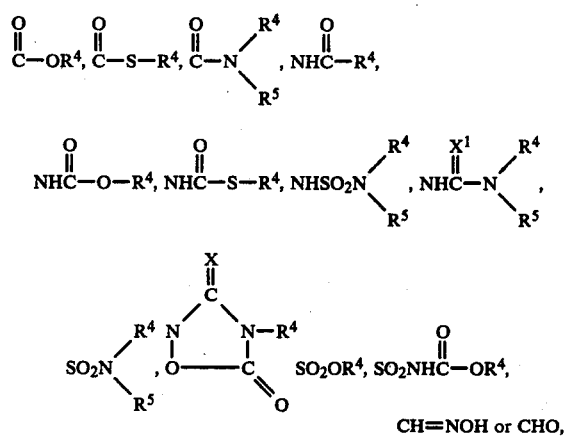

CH=NOH or CHO, or by lower alkoxy-carbo-lower alkoxy, lower alkylmercapto-carbo-lower alkoxy, lower alkoxy-carbo-lower alkylmercapto or lower alkylmercapto-carbo-lower alkylmercapto; or $R^2$ may also denote benzyl which is unsubstituted or substituted by halogen, lower alkyl, halo-lower alkyl, lower alkoxy, halo-lower alkoxy or halo-lower alkylmercapto, $R^3$ is hydrogen, a straight-chain aliphatic radical of 1 to 10 carbon atoms, a cycloaliphatic radical of 3 to 7 carbon atoms, a branched aliphatic radical of 3 to 10 carbon atoms or halogen- or alkoxy-substituted alkyl of 2 to 10 carbon atoms, $R^4$ and $R^5$ are lower alkyl and $R^5$ may also be hydrogen, X and Y are oxygen, sulfur, sulfinyl or sulfonyl and $X^1$ is oxygen or sulfur.

* * * * *